(12) United States Patent
Simpson

(10) Patent No.: US 12,029,458 B2
(45) Date of Patent: Jul. 9, 2024

(54) SURGICAL GUIDES AND IMPLANTS HAVING REGISTRATION MEMBERS

(71) Applicant: Travis Simpson, Jacksonville, FL (US)

(72) Inventor: Travis Simpson, Jacksonville, FL (US)

(73) Assignee: KLS MARTIN, L.P., Jacksonville, FL (US)

( * ) Notice: Subject to any disclaimer, the term of this patent is extended or adjusted under 35 U.S.C. 154(b) by 925 days.

(21) Appl. No.: 17/063,434

(22) Filed: Oct. 5, 2020

(65) Prior Publication Data

US 2021/0100596 A1 Apr. 8, 2021

Related U.S. Application Data

(60) Provisional application No. 62/910,926, filed on Oct. 4, 2019.

(51) Int. Cl.
| | | |
|---|---|---|
| *A61B 17/80* | (2006.01) | |
| *A61B 17/88* | (2006.01) | |
| *A61B 90/00* | (2016.01) | |
| *A61B 17/90* | (2006.01) | |

(52) U.S. Cl.
CPC .......... *A61B 17/8071* (2013.01); *A61B 17/88* (2013.01); *A61B 90/39* (2016.02); *A61B 17/90* (2021.08); *A61B 2090/3983* (2016.02)

(58) Field of Classification Search
CPC ...... A61B 90/39; A61B 17/8071; A61B 17/88
See application file for complete search history.

(56) References Cited

U.S. PATENT DOCUMENTS

2013/0071811 A1\* 3/2013 Groscurth ............ A61C 8/0089
433/75

\* cited by examiner

*Primary Examiner* — Sameh R Boles
(74) *Attorney, Agent, or Firm* — Thomas C. Saitta

(57) ABSTRACT

A surgical guide used in computer-aided orthognathic or similar bone surgery, the guide being structured to properly locate the osteotomy marking members and implant fixation screw-receiving holes on the bone surfaces of the patient, and/or the cutting of the osteotomy or the drilling of implant fixation screw-receiving holes. The guide has a bone-conforming member and a dental-interface member connected by a bridging member, the inner surfaces of the bone-conforming member and the dental interface member conforming to the topographical surfaces of the patient's bone and teeth. The dental-interface member abuts the front and sides of the teeth. A similarly designed fixation implant may also be provided.

8 Claims, 10 Drawing Sheets

SURGICAL GUIDES AND IMPLANTS HAVING REGISTRATION MEMBERS

BACKGROUND OF THE INVENTION

This invention relates generally to osteotomy cutting and drilling guides and bone fixation implants used for example in orthognathic surgery or related bone treatments involving osteotomies or bone repair, and in particular wherein the guides and implants are shaped and configured based on computer-aided design to conform to the surface topography of the bone. More particularly, the invention relates to such guides and implants are provided with registration members or structures to insure proper positioning and alignment of the devices on the bone surfaces, and even more particularly to such guides and implants wherein the registration members abut the For ease of discussion and without intending to limit the field of application, the guides and implants will be discussed primarily in reference to orthognathic surgery, also known as corrective maxillofacial or jaw surgery, which is surgery designed to correct conditions of the jaw and face related to structure, growth, sleep apnea, TMJ disorders, malocclusion problems owing to skeletal disharmonies, or other orthodontic problems that cannot be easily treated with braces. In a typical orthognathic procedure in oral surgery, for example, bone is cut, moved, modified, and realigned to correct a dentofacial deformity. The word "osteotomy" means the division, or excision of bone. The osteotomies may be performed on the maxilla (e.g., a LeFort I), the mandible (e.g., a sagittal split), or the chin (e.g., a genioplasty).

Modern orthognathic surgery makes use of computer-aided design and manufacturing techniques whereby technicians create pre-operative and post-operative 3-D models of a patient, whether virtual or physical, showing the current configuration of the jaw and/or face before surgery and the desired configuration after surgery. Guides for cutting the osteotomy and/or marking the location(s) of the osteotomy on the maxilla, mandible or chin as well as for drilling holes to receive bone fastening screws are manufactured. Fixation implants configured such that when attached to the bone segments after the osteotomy the bone segments will be properly positioned relative to each other are also produced.

The guides conform to the pre-operative configuration of the patient's bone structure, such that the surgeon can easily position the guide in the proper location. The surgeon then uses the guide to mark the location for the osteotomy and either marks or drills holes through apertures in the guide, the holes being properly positioned to receive the bone screws used to fasten the fixation implants to the bone segments with the bone segments positioned in the desired post-operative relationship. Alternatively, rather than using the guides for marking purposes, the guides may be produced with physical structures to guide the osteotomy saw.

One type of guide is referenced as an occlusal guide in that a portion of the guide is designed to abut and rest on the upper surfaces of the teeth. Typically, a guide is manufactured out of a plastic material and a portion of the guide is configured to match or confirm to the surfaces of a plurality of adjacent teeth, typically 4 or 5. This portion is often referred to as a splint and is the portion of the guide that insures proper positioning and alignment. A bridging member then connects the splint to one or more bone-conforming members, the bone-conforming members being configured to conform to a portion of the bone surface on the maxilla, mandible or chin. Because of the computer-aided manufacturing process, the guide cannot be mis-positioned on the patient, as the splint portion will mate with the plurality of teeth only in the single position that properly aligns and locates the one or more bone-conforming members on the bone surfaces. While this occlusal guide structure is useful, the bulkiness of device, and in particular the bulkiness of the splint portion conforming to the teeth surfaces, may interfere with or make difficult the marking of the osteotomy and the drilling of the fixation holes.

Once the osteotomies and screw-receiving holes have been created, the guide is removed and the fixation implants are affixed to the separated bone segments. The fixation implants are produced to conform to the desired post-operative configuration of the patient's bone structure, and in like manner to the guides, the inner surfaces of the implants which abut the patient's tissue are configured to conform to the surface topography of the area onto which they are to be affixed.

While such guides and implants have dramatically improved orthognathic surgery by obviating the need for a surgeon to manipulate a guide or implant by hand to produce a "best fit", there is still room for error in the placement in the positioning of the guide or implant during the procedure, and finding the exact location for proper conformation can still be time consuming. It is an object of this invention therefore to produce guides and implants which reduce the likelihood of mis-positioning, the guides and implants having registration members or structures, wherein the registration members abut the sides of the teeth and fit within the gaps between adjacent teeth.

SUMMARY OF THE INVENTION

In brief summary, the invention in various embodiments is a surgical osteotomy and drilling guide or a bone fixation implant, or the combination of such a guide and implant in a kit, used in computer-aided orthognathic surgery, or similar bone repair or bone modification surgery. The guide is structured to properly locate the osteotomy marking members and implant fixation screw-receiving holes on the bone surfaces of the patient, and/or the cutting of the osteotomy or the drilling of implant fixation screw-receiving holes. The guide comprises at least one registration or dental-interface member configured to reside in the gap or valley formed between the exposed lateral portions of adjacent teeth, one or more bone-conforming members configured to conform to the bone surface topography of the maxilla, mandible or chin, and one or more bridging members connecting the one or more bone-conforming members to the dental-interface member, the bone-conforming members comprising the drill guide apertures and the osteotomy marking or cutting surfaces. The implant is structured to properly locate a bone-conforming member on the bone segments after an osteotomy has been performed, the implant comprising at least one registration or dental-interface member configured to reside in the gap or valley formed between the exposed lateral portions of adjacent teeth and one or more bridging members connecting the dental-interface member to the bone-conforming member, the one or more bridging members and at least one dental-interface member being structured such that they may be removed from the bone-conforming member after it has been affixed to the bone segments.

In one embodiment the dental-interface member is a generally U-shaped or semicircular member positioned about a single tooth, the dental-interface member configured to abut against the facial or buccal (i.e., frontal outer) surface of the exposed tooth crown and having a pair of curved or hooked arm members which reside adjacent to and abutting the mesial and distal (i.e., lateral to the middle and lateral to the rear, respectively) surfaces of the exposed tooth crown. In an alternative embodiment, the guide and implant have one or more dental-interface members, each of which is mounted on a dedicated bridging member, wherein instead of encompassing a single tooth the dental-interface member is configured to abut the mesial, facial and distal side of the crown of a first tooth and the mesial, facial and distal side of the crown of a second, adjacent tooth.

Through computer-aided design, the dental-interface member or members have an inner tooth-conforming surface that conforms to the exposed crown surface. In this manner there is only a singular position for the dental-interface member that correctly mates and aligns with the tooth crown, thereby insuring proper placement and positioning of the bone-conforming member of the guide or implant.

In alternative summary, the invention is a surgical osteotomy and drilling guide configured by computer-aided design comprising: at least one bone-conforming member having a bone-conforming inner surface conforming to the surface topography of a bone of a patient, the at least one bone-conforming member comprising an osteotomy marking or cutting structure and drill guide apertures; at least one dental-interface member having a tooth-conforming inner surface conforming to the surface topography of a tooth of the patient, the at least one dental-interface member adapted to laterally abut the facial, mesial and distal sides but not the upper surface of the tooth of the patient; and a bridging member connecting the bone-conforming member to the dental-interface member; wherein the at least one bone-conforming inner surface and the at least one tooth-conforming inner surface are customized to fit the patient. Furthermore, the invention wherein the at least one dental-interface member comprises a U-shaped main body, a pair of arm members and a facial abutting portion; wherein the at least one dental-interface member comprises a W-shaped main body, a mesial abutting portion, a distal abutting portion, a central gap abutting portion, and first and second facial abutting portions; further comprising an extension arm and abutment member extending from the mesial portion; and/or wherein the at least one dental-interface member consists of two dental-interface members.

Furthermore, the invention is a kit comprising the guide and a bone fixation implant configured by computer-aided design, the implant comprising: at least one implant bone-conforming member having an implant bone-conforming inner surface conforming to the surface topography of the bone of the patient; at least one implant dental-interface member having an implant tooth-conforming inner surface conforming to the surface topography of the tooth of the patient, the at least one implant dental-interface member adapted to laterally abut the facial, mesial and distal sides but not the upper surface of the tooth of the patient; and an implant bridging member connecting the implant bone-conforming member to the implant dental-interface member; wherein the at least one implant bone-conforming inner surface and the at least one implant tooth-conforming inner surface are customized to fit the patient. Furthermore, such invention wherein the at least one dental-interface member comprises a U-shaped main body, a pair of arm members and a facial abutting portion, and wherein the at least one implant dental-interface member comprises a U-shaped main body, a pair of arm members and a facial abutting portion; wherein the at least one dental-interface member comprises a W-shaped main body, a mesial abutting portion, a distal abutting portion, a central gap abutting portion, and first and second facial abutting portions, and wherein the at least one implant dental-interface member comprises a W-shaped main body, a mesial abutting portion, a distal abutting portion, a central gap abutting portion, and first and second facial abutting portions; further comprising an extension arm and abutment member extending from the mesial portion, and the implant further comprising an extension arm and abutment member extending from the mesial portion; and/or wherein the at least one dental-interface member consists of two dental-interface members, and the implant wherein the at least one implant dental-interface member consists of two implant dental-interface members.

DETAILED DESCRIPTION OF THE INVENTION

Figure 1:
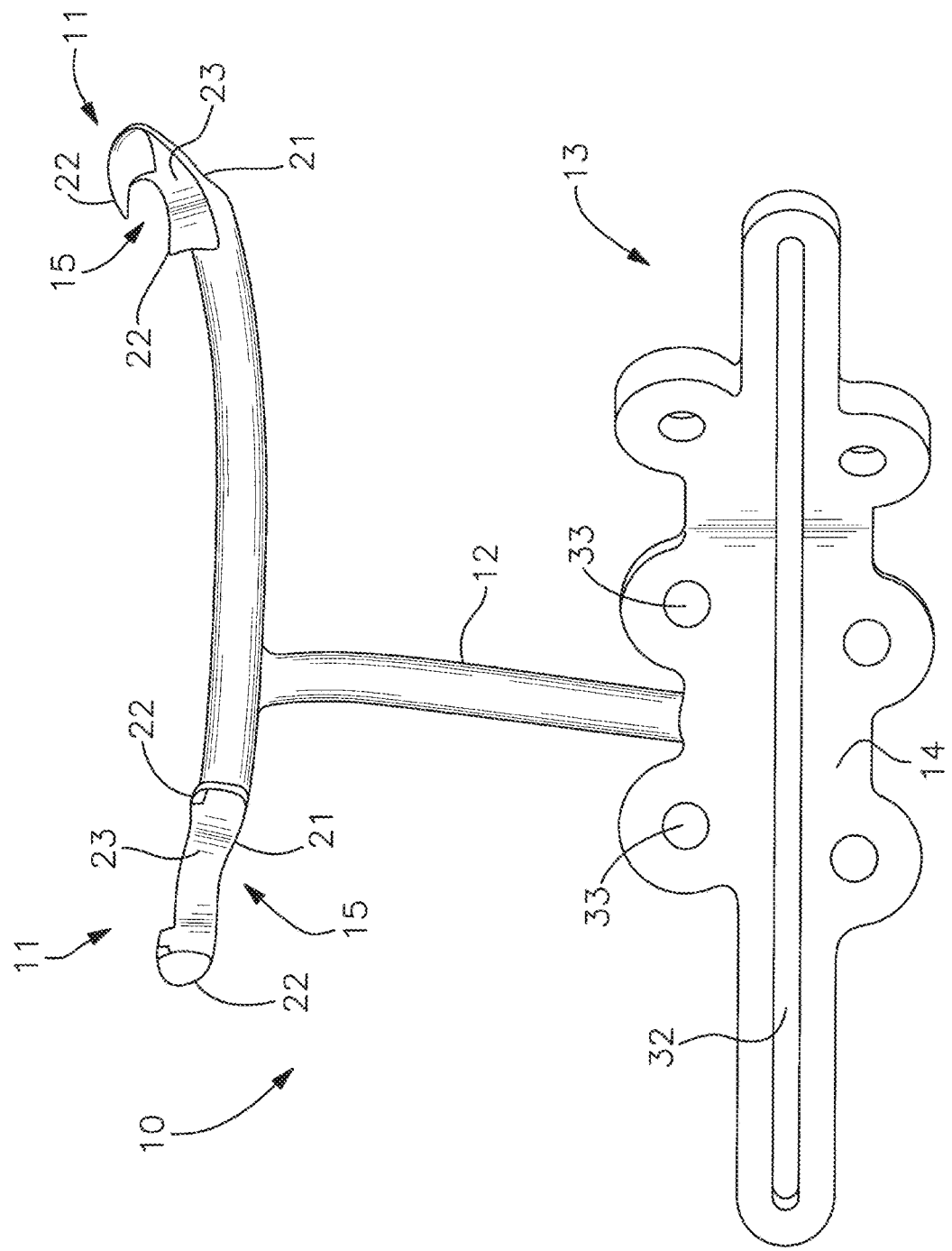
FIG. 1 illustrates the interior side of one embodiment of the guide, the guide being configured as a genioplasty guide and having a pair of dental-interface members, each of which is structured to abut a single, non-adjacent tooth on the facial, mesial and distal surfaces.

In general, the invention in various embodiments is a customized surgical guide 10 or bone fixation implant 50, alone or in a kit, used in computer-aided orthognathic surgery, or similar bone repair or bone modification surgery, the guide 10 or implant 50 comprising a bone-conforming member or plate 13 and a registration or dental-interface member 11 connected by a bridging member 12.

The bone-conforming member 13 comprises a bone-conforming inner surface 14 created and configured through computer-aided design that conforms to the bone surface topography of a particular patient at the desired placement location on the bone or tissue of the patient. The bone-conforming member 13 of guide 10 further comprises an osteotomy marking or cutting structure 32, such as an edge or a slot, and/or drill guide apertures 33.

The dental-interface member 11 comprises a tooth-conforming inner surface 15 created and configured through computer-aided design to laterally abut the front and sides of the exposed surfaces of a tooth 91 (i.e., facial, mesial and distal sides) or adjacent teeth 91 of the particular patient. In one embodiment the dental-interface member 11 may comprise a generally U-shaped main body 21 with opposing arm members 22 and a facial abutting portion 23, for abutment with a single tooth 91. In other embodiments the dental-interface member 11 may comprise a generally W-shaped main body 40 with a central gap abutting portion 43, a mesial abutting portion 41, a distal abutting portion 42, and first and second facial abutting portions 44/45, and possibly an extension portion 46 extending across a missing tooth gap to another tooth 91. The arm members 22, central gap abutting portions 43, mesial abutting portions 41, and distal abutting portions 42 are sized and configured so as not to envelop or encircle the back half of the teeth 91, such that these elements can be inserted into only the front portion of the gap or valley between adjacent teeth 91 a sufficient distance to properly register or locate the bone-conforming member 13. In this manner the dental-interface member 11 abuts the tooth or teeth 91 but does not grip or retain the tooth 91, and can be easily retraced from the tooth 91.

The bridging member 12 may be configured to serve as a grip or handle. For an implant 50, the bridging member 12 is sized, configured and composed of a material that enables easy separation of the bridging member 12 and dental-interface member 11 once the body-conforming member 13 has been affixed to the bone segments.

Figure 2:
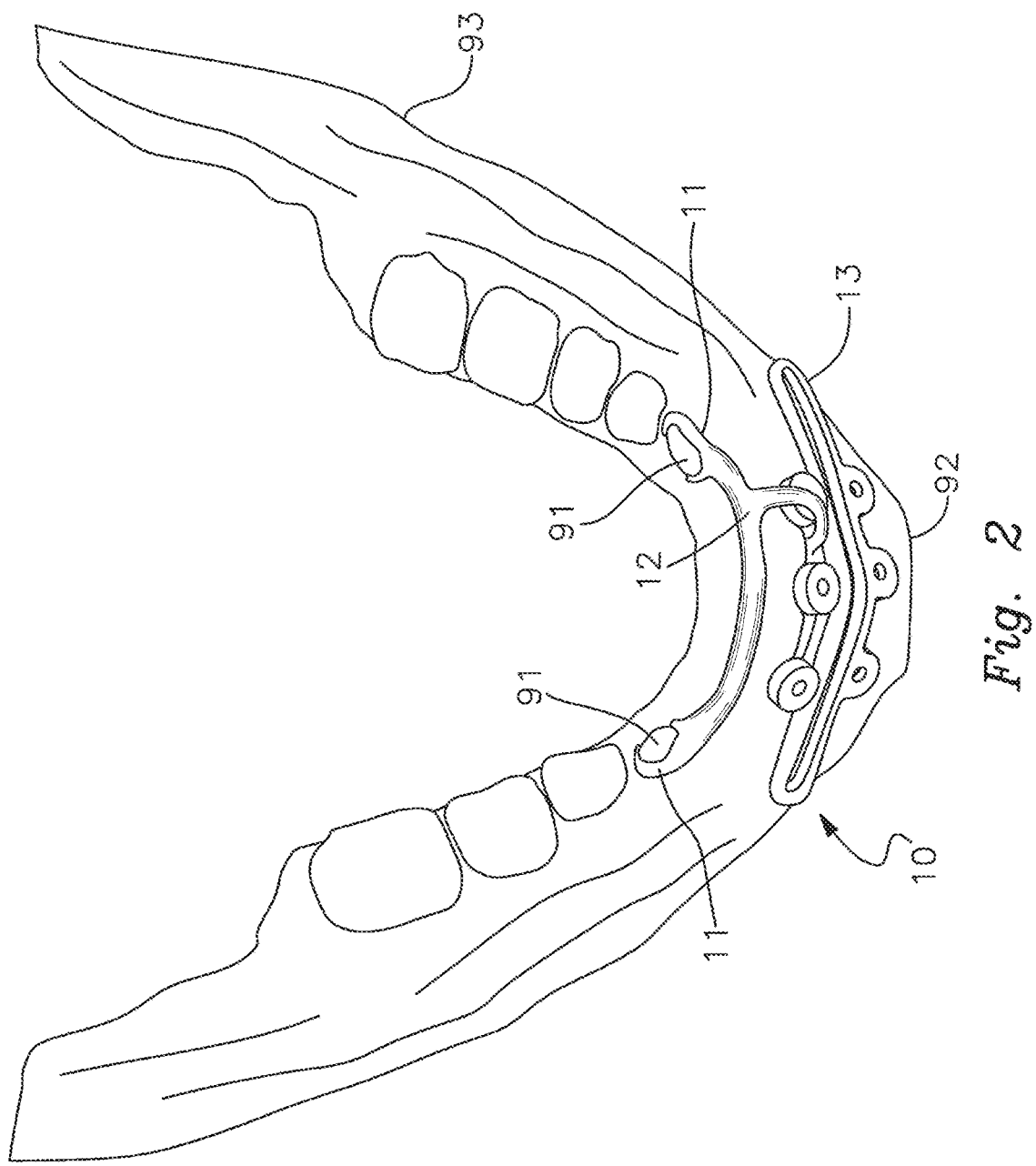
FIG. 2 is a view of the guide of FIG. 1 as positioned on a mandible.
Figure 3:
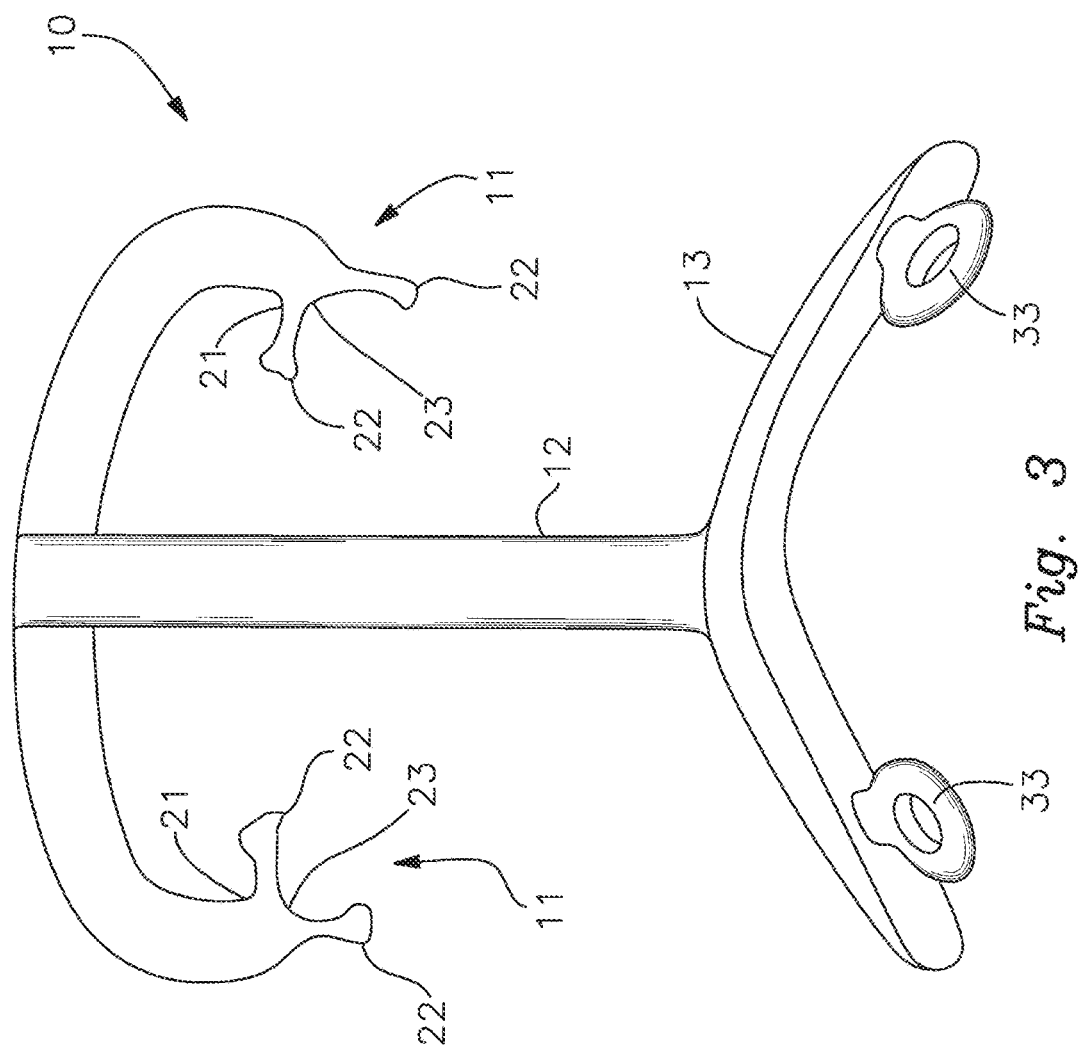
FIG. 3 is a perspective view of a guide similar to the embodiment of FIG. 1.
Figure 4:
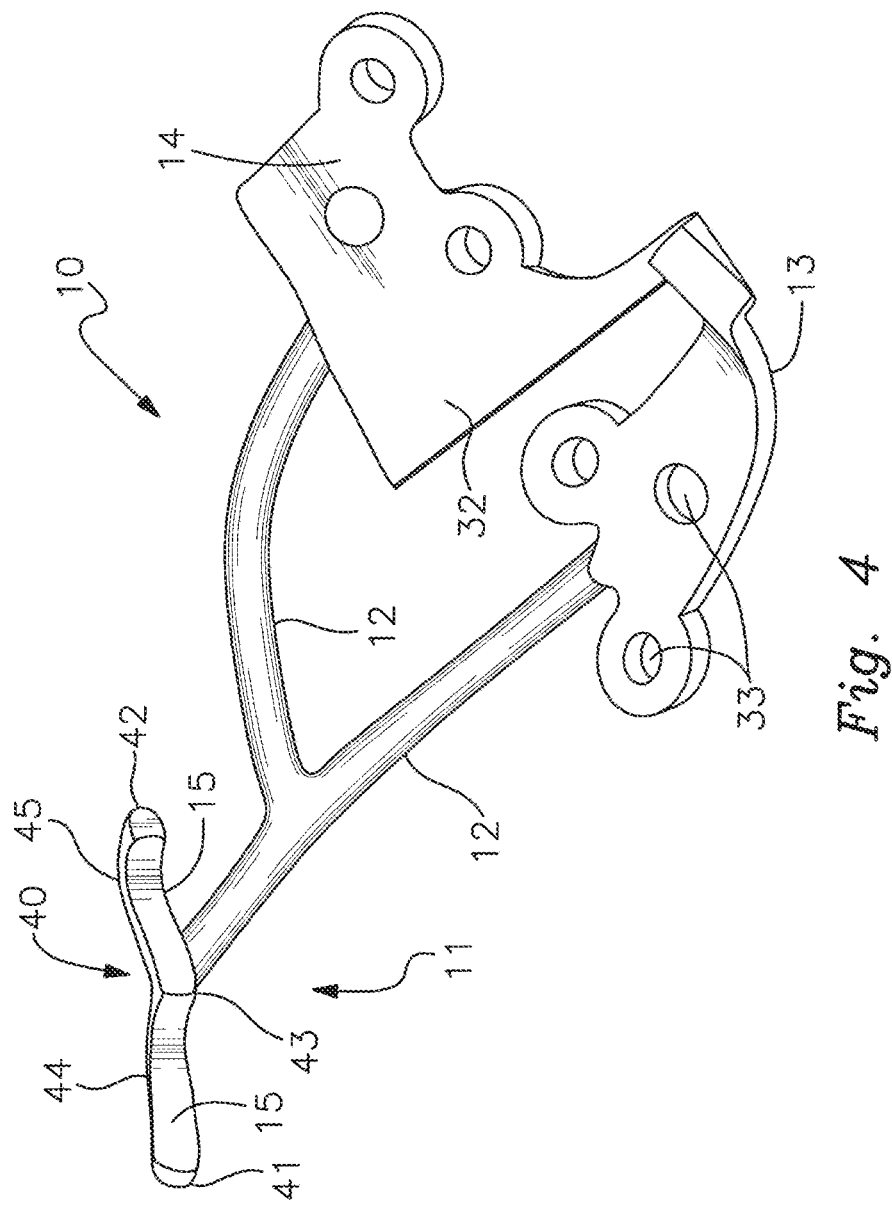
FIG. 4 illustrates the interior side of an alternative embodiment of the guide, the guide being configured as a mandibular guide and having a dental-interface member structured to abut two adjacent teeth.

In one representative embodiment for a surgical guide 10, shown as a genioplasty (chin) guide in FIGS. 1 through 3, the dental-interface member 11 has a generally U-shaped or semicircular body 21 positioned about a single tooth, the dental-interface member 11 having a facial abutting portion 23 configured to abut against the facial or buccal (i.e., frontal outer) surface of the tooth crown 91 and having a pair of curved or hooked arm members 22 which reside adjacent to and abutting the mesial and distal (i.e., lateral) surfaces of the tooth 91. The combination of the arm members 22 and facial abutting portion 23 define a tooth-conforming inner surface 15 that because of computer-aided design conforms to the surface topography of the tooth 91 to which it is abutted. This feature in combination with the bone-conforming inner surface 14, also created by computer-aided design, insures that the guide 10 will properly positioned for the marking or cutting of the bone.

Figure 5:
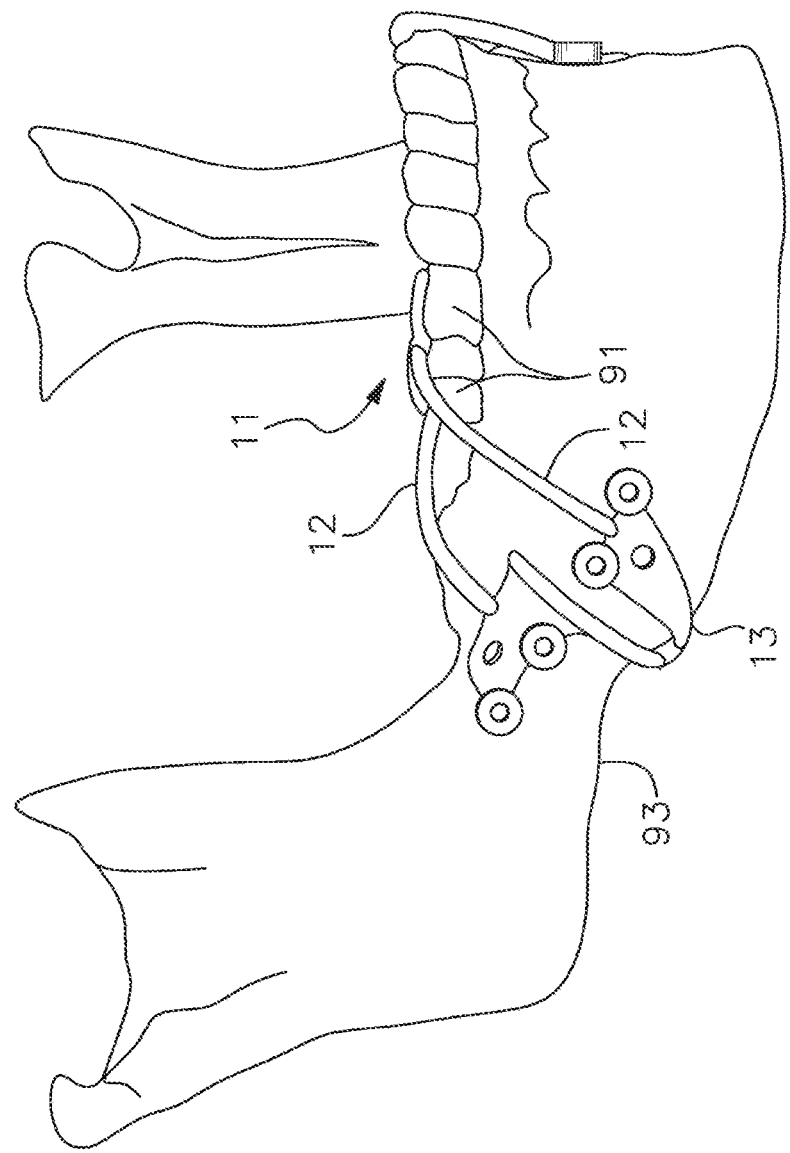
FIG. 5 is a view of the exterior side of the guide of FIG. 4 as positioned on a mandible.
Figure 6:
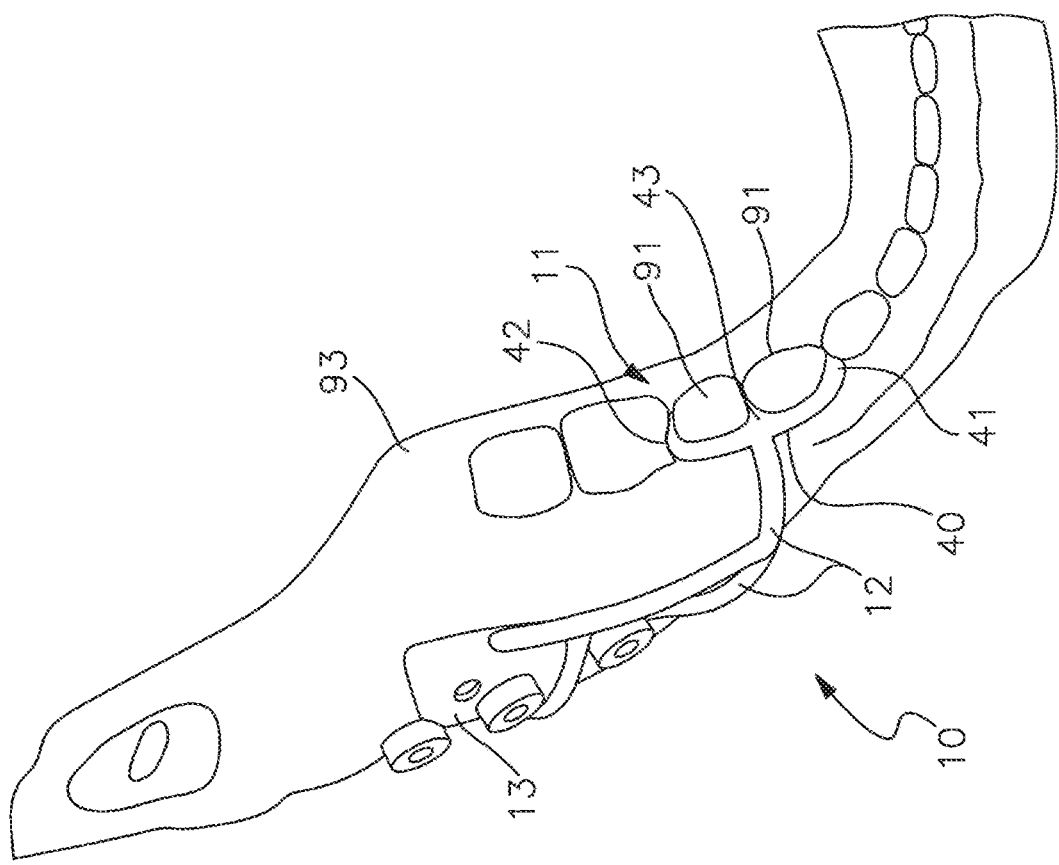
FIG. 6 is a view of the upper side of the guide of FIG. 4 as positioned on a mandible.

In an alternative embodiment, shown as a mandibular guide 10 in FIGS. 4 through 7, the guide 10 has a dental-interface member 11 comprising a W-shaped main body 40 adapted to abut adjoining teeth 91. The W-shaped main body 40 comprises a pair of tooth-conforming surfaces 15, one defined by the combination of a mesial abutting portion 41, a first facial abutting portion 44 and a central gap abutting portion 43, and the other defined by the central gap abutting portion 43, a second facial abutting portion 45 and a distal abutting portion 42. The dental-interface member 11 is connected to a bone-conforming member 13 by a pair of bridging members 12, the bone-conforming member 13 comprising a bone-conforming inner surface 14, an osteotomy marking or cutting structure 32 and drill guide apertures 33. As shown in FIGS. 5 and 6, the dental-interface member 11 abuts the front side of a pair of adjoining teeth 91 such that the central gap abutting portion 43 rests between the two teeth 31, the distal abutting portion 42 abuts the distal side of the most distal tooth, the mesial abutting portion 41 abuts the mesial side of the most mesial tooth 91, and the two facial abutting portions 44/45 conform and abut to the facial surfaces of the teeth 91. The mesial abutting portion 41, central gap abutting portion 43 and distal abutting portion 42 extend less than halfway into the gaps between the teeth 91, such that placement and removal is easily accomplished. The combination of the tooth-conforming inner surfaces 15 of the dental-interface member 11 and the bone-conforming inner surfaces 14 of the bone-conforming member 11, further in combination with the relative configuration of the dental-interface member 11, bridging member 12 and bone-conforming member 13, all designed and manufactured through computer-aided design to match the surface topography of the bones and teeth of the patient, provide for the stable and fixed placement of the guide 10.

Figure 7:
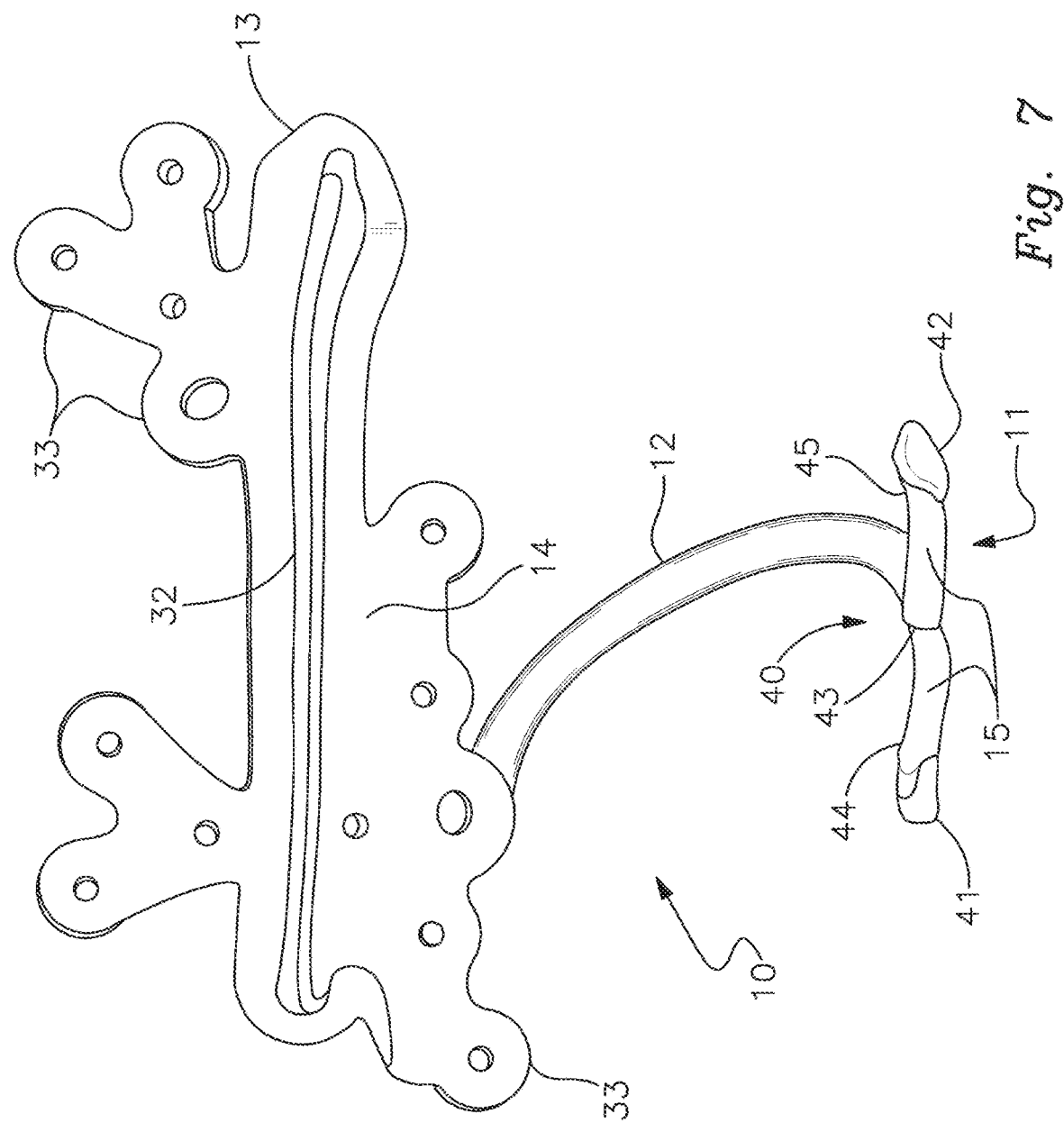
FIG. 7 illustrates the interior side of an alternative embodiment of the guide, the guide being configured as a maxillary guide and having a dental-interface member structured to abut two adjacent teeth.
Figure 8:
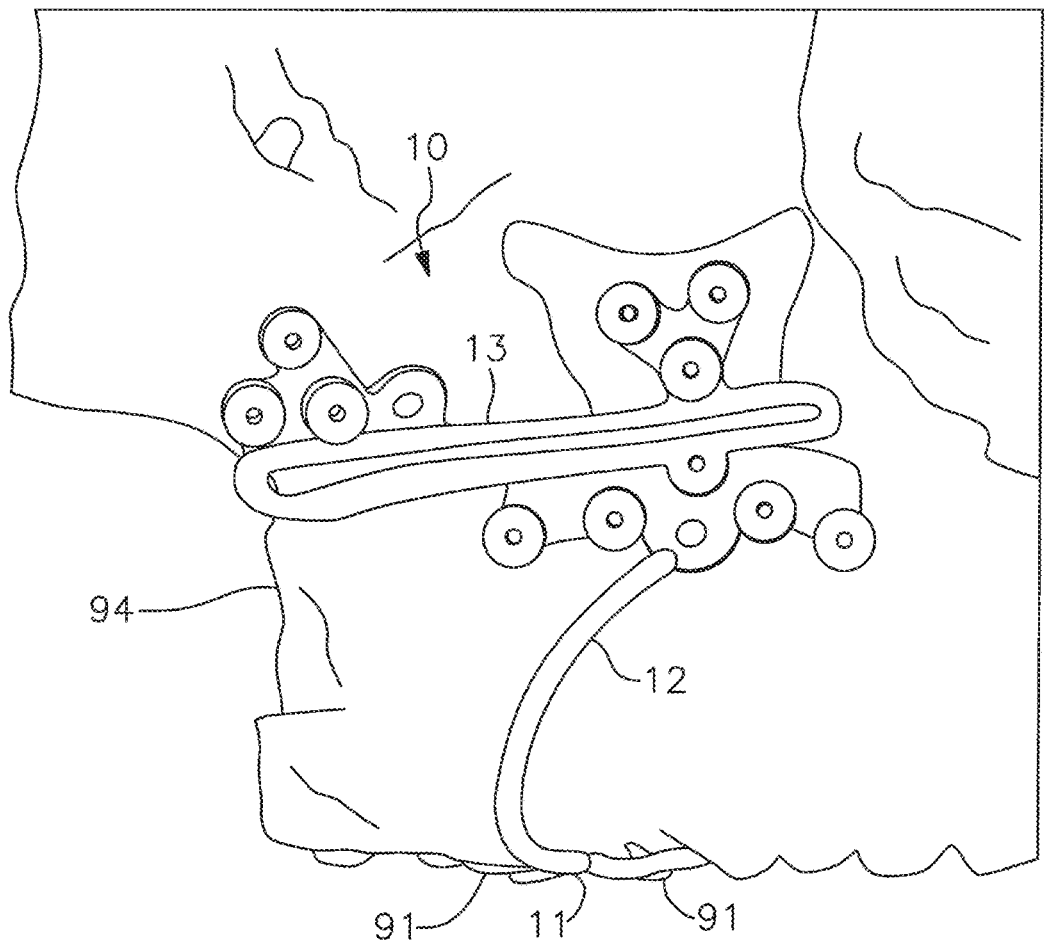
FIG. 8 is a view of the exterior side of the guide of FIG. 4 as positioned on a maxilla.

Still another embodiment is depicted in FIGS. 7 and 8, which in this case is a maxillary guide 10. It is structurally similar to the mandibular guide 10, comprising a dental-interface member 11 and bone-conforming member 13 connected by a bridging member 12. The guide 10 has a dental-interface member 11 comprising a W-shaped main body 40 adapted to abut adjoining teeth 91. The W-shaped main body 40 comprises a pair of tooth-conforming surfaces 15, one defined by the combination of a mesial abutting portion 41, a first facial abutting portion 44 and a central gap abutting portion 43, and the other defined by the central gap abutting portion 43, a second facial abutting portion 45 and a distal abutting portion 42. The dental-interface member 11 is connected to a bone-conforming member 13 by a pair of bridging members 12, the bone-conforming member 13 comprising a bone-conforming inner surface 14, an osteotomy marking or cutting structure 32 and drill guide apertures 33. the dental-interface member 11 abuts the front side of a pair of adjoining teeth 91 such that the central gap abutting portion 43 rests between the two teeth 31, the distal abutting portion 42 abuts the distal side of the most distal tooth, the mesial abutting portion 41 abuts the mesial side of the most mesial tooth 91, and the two facial abutting portions 44/45 conform and abut to the facial surfaces of the teeth 91. The mesial abutting portion 41, central gap abutting portion 43 and distal abutting portion 42 extend less than halfway into the gaps between the teeth 91, such that placement and removal is easily accomplished. The combination of the tooth-conforming inner surfaces 15 of the dental-interface member 11 and the bone-conforming inner surfaces 14 of the bone-conforming member 11, further in combination with the relative configuration of the dental-interface member 11, bridging member 12 and bone-conforming member 13, all designed and manufactured through computer-aided design to match the surface topography of the bones and teeth of the patient, provide for the stable and fixed placement of the guide 10.

Figure 9:
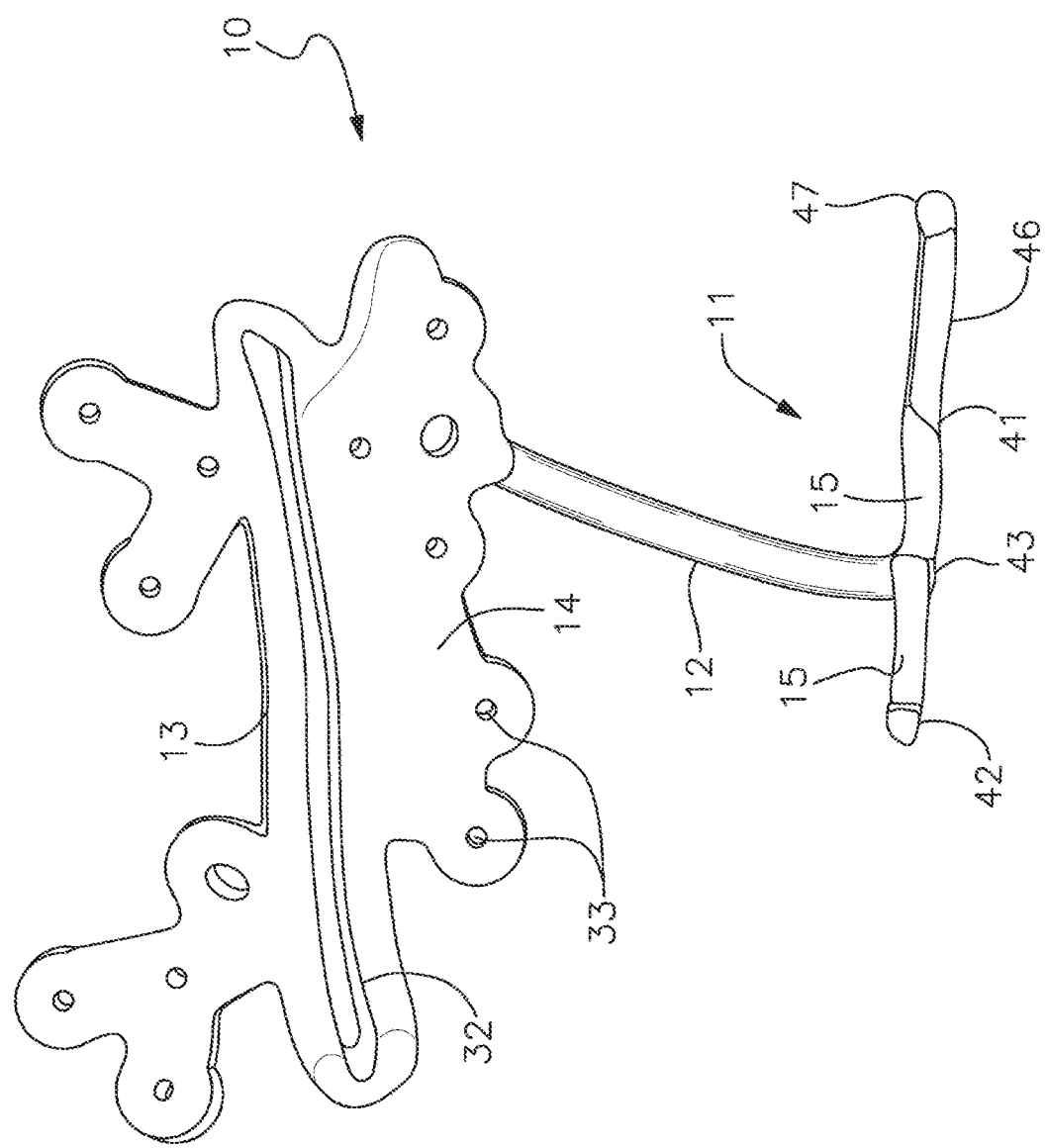
FIG. 9 illustrates the interior side of an alternative embodiment of the guide, the guide being configured as a maxillary guide and having a dental-interface member structured to abut two adjacent teeth and extend across a gap to a third tooth.
Figure 10:
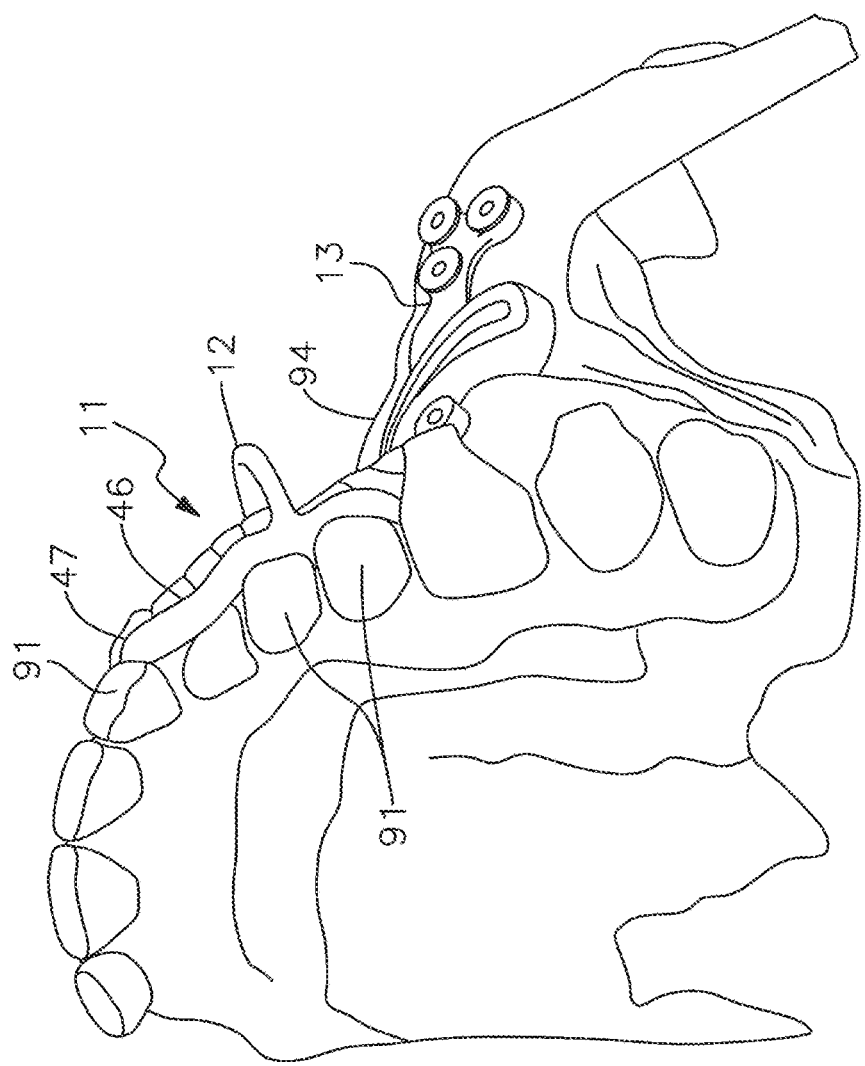
FIG. 10 is a view of the guide of FIG. 9 as positioned on a maxilla.

FIGS. 9 and 10 illustrate another embodiment of a guide 10, in this case a maxillary guide similar to the maxillary guide illustrated in FIGS. 7 and 8. In this embodiment, the dental-interface member 11 comprises a dental-interface member 11 comprising a W-shaped main body 40 adapted to abut adjoining teeth 91. The W-shaped main body 40 comprises a pair of tooth-conforming surfaces 15, one defined by the combination of a mesial abutting portion 41, a first facial abutting portion 44 and a central gap abutting portion 43, and the other defined by the central gap abutting portion 43, a second facial abutting portion 45 and a distal abutting portion 42, and further comprises an extension arm 46 extending from the mesial abutting portion 41, the extension arm 41 ending in an abutment shoulder 47. This embodiment is suitable for circumstances where one or more teeth or missing, such that the extension arm 46 crosses the gap such that the abutment shoulder 47 can abut the next proximal tooth 91 to better stabilize the guide 10.

A bone fixation implant 50 is designed and manufactured through computer-aided methods in similar manner to the guide 10 such that the bone-conforming member 13 and the dental-interface member 11 have, respectively, a bone-conforming inner surface 14 and a tooth-conforming inner surface 15, and are connected by one or more bridging members 12. The difference is that the bone-conforming member 12 of the implant 50 is not provided with an osteotomy marking or cutting structure, since the osteotomy has been performed prior to fixation of the bone-conforming member 13 to the patient's bone segments. Once affixed, the bridging member 12 and dental-interface member 11 is cut or otherwise separated from bone-conforming member 13 and removed.

Because of the reduced structure of the dental-interface member 11 in comparison to the splint portion of the plastic guides, it is necessary to produce the guides 10 of the invention in a much more rigid material, such as titanium for example.

To use the guide 10, the surgeon positions the dental-interface member or members 11 on the crown or crowns such that the bone-conforming member rests on the bone surface of the maxilla, mandible or chin. The surgeon marks the osteotomy location using the marking/cutting edge 31 and marks the location for the bone screw receiving holes, or alternatively drills the holes using the drill guide apertures 33. Alternatively, the surgeon may first mark or drill the holes using the drill guide apertures 33 and then use the marking/cutting edge 31 to perform the osteotomy. The guide 10 is then removed from the patient, the bone segments repositioned into the desired configuration, and the fixation implant 50 is affixed to the bone segments. The bridging member 12 and dental-interface member 11 is cut or otherwise separated from bone-conforming member 13 and removed.

I claim:

1. A surgical osteotomy and drilling guide configured by computer-aided design to conform to a bone and to a tooth of a patient, the bone having a surface topography and the tooth having a surface topography, a facial side, a mesial side, a distal side and an upper surface, the surgical osteotomy and drilling guide comprising:

at least one bone-conforming member having a bone-conforming inner surface configured to conform to the surface topography of the bone of the patient, the at least one bone-conforming member comprising an osteotomy marking or cutting structure and drill guide apertures;

at least one dental-interface member having a tooth-conforming inner surface configured to conform to the surface topography of the tooth of the patient, the at least one dental-interface member adapted to laterally abut the facial side, the mesial side and the distal side but not the upper surface of the tooth of the patient; and a bridging member connecting the at least one bone-conforming member to the at least one dental-interface member;

wherein the at least one bone conforming inner surface is customized to fit the surface topography of the bone of the patient and the at least one tooth-conforming inner surface is customized to fit the surface topography of the tooth of the patient.

2. The guide of claim 1, wherein the at least one dental-interface member comprises a U-shaped main body, a pair of arm members and a facial abutting portion.

3. The guide of claim 2 wherein the at least one dental-interface member consists of two dental-interface members.

4. The guide of claim 2, wherein the guide is a unitary member.

5. The guide of claim 1, wherein the at least one dental-interface member comprises a W-shaped main body, a mesial abutting portion, a distal abutting portion, a central gap abutting portion, and first and second facial abutting portions.

6. The guide of claim 5, further comprising an extension arm and abutment member extending from the mesial portion.

7. The guide of claim 5, wherein the guide is a unitary member.

8. The guide of claim 1, wherein the guide is a unitary member.

* * * * *